US009442085B2

(12) United States Patent
Peterson et al.

(10) Patent No.: US 9,442,085 B2
(45) Date of Patent: *Sep. 13, 2016

(54) METHOD FOR ANALYSIS USING X-RAY FLUORESCENCE

(71) Applicant: ICAGEN, INC., Durham, NC (US)

(72) Inventors: Lori J. Peterson, Los Alamos, NM (US); Cameron A. Mortillaro, Phoenix, AZ (US); Benjamin P. Warner, Los Alamos, NM (US); Nathan H. Zahler, Ashland, MA (US); Pratima Bharti, Portage, MI (US); Chang-Tai Hsieh, Chestnut Hill, MA (US); Emilia A. Solomon, Los Alamos, NM (US)

(73) Assignee: ICAGEN, INC., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/715,218

(22) Filed: May 18, 2015

(65) Prior Publication Data

US 2015/0276632 A1 Oct. 1, 2015

Related U.S. Application Data

(63) Continuation of application No. 13/317,341, filed on Oct. 14, 2011, now Pat. No. 9,063,066.

(60) Provisional application No. 61/455,030, filed on Oct. 14, 2010.

(51) Int. Cl.
| | |
|---|---|
| *G01N 23/223* | (2006.01) |
| *G01N 33/483* | (2006.01) |
| *G01N 33/487* | (2006.01) |
| *A61B 6/00* | (2006.01) |

(52) U.S. Cl.
CPC .......... *G01N 23/223* (2013.01); *G01N 33/487* (2013.01); *G01N 33/4833* (2013.01); *A61B 6/485* (2013.01); *G01N 2223/076* (2013.01); *G01N 2223/0766* (2013.01); *G01N 2223/6126* (2013.01)

(58) Field of Classification Search
CPC .... A61B 6/03; A61B 6/485; G01N 23/2202; G01N 23/2208; G01N 23/223; G01N 2223/076; G01N 2223/0766; G01N 2203/612; G01N 2203/6126
See application file for complete search history.

(56) References Cited

U.S. PATENT DOCUMENTS

| | | | | |
|---|---|---|---|---|
| 4,577,337 | A | | 3/1986 | Light |
| 4,717,826 | A | * | 1/1988 | Silver ................ G01N 23/2252 250/307 |
| 5,574,284 | A | | 11/1996 | Farr |
| 5,778,039 | A | | 7/1998 | Hossain |

(Continued)

OTHER PUBLICATIONS

Aoki et al., "Imaging X-ray fluorescence microscope wiht a Wolter-type grazing-incidence mirror," J. Synchrotron Rad. 5:1117-1118 (1998).

(Continued)

*Primary Examiner* — Thomas R Artman
(74) *Attorney, Agent, or Firm* — Morgan, Lewis & Bockius LLP

(57) ABSTRACT

The present invention is a method to quantify biomarkers. The method uses an X-ray fluorescence spectrometer to perform an X-ray fluorescence analysis on the sample to obtain spectral features derived from the biomarker; and quantifying the X-ray fluorescence signal of the biomarker.

23 Claims, 15 Drawing Sheets

(56) References Cited

U.S. PATENT DOCUMENTS

| | | | |
|---|---|---|---|
| 6,858,148 B2 | 2/2005 | Warner | |
| 7,519,145 B2 * | 4/2009 | Warner | G01N 23/223 378/47 |
| 7,688,943 B2 * | 3/2010 | Chikawa | G01N 23/223 378/44 |
| 7,858,385 B2 | 12/2010 | Warner | |
| 7,929,662 B2 * | 4/2011 | Warner | G01N 23/223 378/47 |
| 8,238,515 B2 | 8/2012 | Birnbaum | |
| 8,431,357 B2 | 4/2013 | Birnbaum | |
| 9,063,066 B2 * | 6/2015 | Peterson | G01N 23/223 |
| 2004/0235059 A1 | 11/2004 | Warner | |
| 2007/0258561 A1 * | 11/2007 | Chikawa | G01N 23/223 378/45 |
| 2008/0220441 A1 * | 9/2008 | Birnbaum | G01N 33/566 435/7.1 |
| 2009/0087919 A1 | 4/2009 | Birnbaum | |
| 2010/0299766 A1 * | 11/2010 | Demuth | A01K 67/0276 800/3 |
| 2012/0093286 A1 * | 4/2012 | Peterson | G01N 23/223 378/45 |
| 2015/0260664 A1 * | 9/2015 | Peterson | G01N 23/223 378/47 |
| 2015/0276631 A1 * | 10/2015 | Peterson | G01N 23/223 378/20 |
| 2015/0276632 A1 * | 10/2015 | Peterson | G01N 23/223 378/20 |

OTHER PUBLICATIONS

Chikara Ohtsuki, "How to prepare the simulated body fluid (SBF) and its related solutions, proposed by Kokubo and his colleagues-" accessed online Apr. 14, 2015.

* cited by examiner

METHOD FOR ANALYSIS USING X-RAY FLUORESCENCE

RELATED APPLICATION/CLAIM OF PRIORITY

This application is a continuation of U.S. application Ser. No. 13/317,341 filed Oct. 14, 2011, which claims priority from provisional application Ser. No. 61/455,030, filed Oct. 14, 2010, the forgoing applications are incorporated by reference herein.

GOVERNMENT RIGHTS

This invention was made with US Government support under contract R44 ES016395 awarded by the National Institute of Health. The Government has certain rights to this invention.

FIELD OF THE INVENTION

The present invention relates to the analysis of specimens using X-ray fluorescence.

BACKGROUND OF THE INVENTION

X-ray fluorescence (XRF) spectrometry is a powerful spectroscopic technique that has been used to determine the elements that are present in a sample, and to determine the quantity of those elements in the sample. The underlying physical principle of the method is that when an atom of a particular element is irradiated with X-ray radiation, the atom ejects a core electron such as a K shell electron. The resulting atom is then in an excited state, and it can return to the ground state by replacing the ejected electron with an electron from a higher energy orbital. This is accompanied by the emission of a photon. The energy of the emitted photons is equal to the difference in the energies of the two orbitals. Each element has a characteristic set of orbital energies and therefore, a characteristic X-ray fluorescence (XRF) spectrum.

An X-ray fluorescence spectrometer is an apparatus capable of irradiating a sample with an X-ray beam, detecting the X-ray fluorescence from the sample, and using the X-ray fluorescence to determine which elements are present in the sample and measuring the quantity of these elements. A typical, commercially available energy dispersive X-ray fluorescence spectrometer is the EDAX Eagle XPL energy dispersive X-ray fluorescence spectrometer, equipped with a microfocus X-ray tube, lithium drifted silicon solid-state detector, processing electronics, and vendor supplied operating software, available from the EDAX division of Ametek, 91 McKee Drive Mahwah, N.J. 07430. An example of a wavelength dispersive X-ray fluorescence spectrometer is the ZSX Primus, available from Rigaku Americas, 9009 New Trails Drive, The Woodlands, Tex. 77381. In principle, any element may be detected and quantified with X-ray fluorescence.

More than 10% of cancer cases and up to 40% of emergency room cases involve misdiagnosis. Better analysis methods are needed. As an example, survival is associated with tumor thickness at the time of melanoma skin cancer diagnosis. The World Health Organization reports that the number of melanoma cases worldwide is increasing faster than any other cancer. An estimated 62,480 new cases and 8,420 deaths from melanoma occurred in the US in 2008. It is estimated that one in 82 people will develop melanoma in their lifetime. Melanoma has the lowest overall survival rate of any skin cancer and the prognosis for patients with metastases is extremely poor, despite a variety of therapies. Metastatic melanoma is highly resistant to current therapies. The risk of death from melanoma increases as the depth of the melanoma increases. If a melanoma is less than 1 millimeter deep, there is a slight chance that it has metastasized. Chances are greater if a melanoma has grown thicker than 1.5 millimeters, i.e. a Breslow thickness of greater than 1.5 mm Early recognition and correct prognosis of melanoma is extremely important in improving survival probability, with 10-year disease-free survival rates exceeding 90% upon early and correct diagnosis. As a second example, Autism Spectrum Disorder (ASD) and Alzheimer's Disease (AD) are thought to involve metal dyshomeostatis; however, adequate biomarkers do not exist for these diseases. Diagnoses are performed with questionnaires after symptoms have already appeared, possibly well after the time when therapies might be beneficial.

One method for estimating cancer prognosis is the use of staging-based analysis, which is the assessment of how much a cancer has spread. Staging systems account for tumor size, whether the tumor has invaded adjacent or distant organs, and whether metastases exist. The stage at the time of diagnosis is a powerful predictor of survival; although, staging methods are often inadequate. In addition, treatments are selected based on the stage of a cancer. Inadequate diagnosis, staging, prognosis, and response to therapy most assuredly harm human health. For example, the "Breslow Depth" is a technique used for the staging and prognosis of melanoma. It may help to predict the presence of lymph node metastasis. However, it is subject to several sources of error. Misdiagnosis and inadequate prognostics may cause patients to receive incorrect medications and additional invasive procedures.

Scientists are striving to find better diagnostic, prognostic, and response biomarkers. For example, prognostic factors that are either currently used or are being assessed as melanoma diagnostics/prognostics include: standard histology, immunostaining, cell type assessment and counting, Breslow depth, Clarks level, level and depth of invasion, mitotic rate, analysis of tumor-infiltrating lymphocytes, analysis of microscopic satellites. All of these face difficulties and inadequacies.

Breslow depth is measured with an ocular micrometer and requires that the entire tumor be excised; it is prone to inaccuracies and several sources of error including subjective decisions by experts, variation and uniformity of staging that is not reproducible because of variations in the depth of layers of the skin, imprecision of surgical margins, and variability in tissue samples. Distinguishing between benign lesions and melanomas is very difficult. An independent review by multiple pathologists is recommended, but agreement between pathologists is considerably variable, with disagreements in up to 40% of diagnoses as examined by panels of experienced dermatopathologists. It is particularly difficult to distinguish melanoma from sun-damaged skin. Specimens obtained using other biopsy techniques (e.g., punch biopsy) are even less accurate and can lead to sampling error. Diagnostic and management problems arise when the initial biopsy does not sample the complete skin thickness or when large lesions are not sampled adequately.

Traditional histochemical staining has been used for many years for disease diagnostics. It is performed by pathologists. Pathologist opinion of structures in stained tissue is the definitive diagnosis for most cancers and is used for prognosis, staging, therapy decisions, drug development, epidemiology, and public policy; it has been used for over 150 years and no automated method has thus far proven to be acceptable. This lack of automation leads to heavy workloads for pathologists, increased costs, and numerous errors. Although histopathologic evaluation is essential for clinical investigation, it remains a time consuming and subjective technique, with unsatisfactory levels of inter- and intra-observer discrepancy.

Mitotic Rate has been explored as a prognostic indicator for tumors such as melanoma in studies. However, mitotic rates vary even within tumors, and sampling can therefore be a major issue. Mitotic rate has been linked to tumor thickness in multivariate analysis, but remained an independent variable in other studies. Clinical usage has not proven worthy.

Mast cell participation in immune responses, tumor progression, and vascularization has been studied in vitro. However, in situ investigation of mast cells in routinely processed tissues is hampered by difficulty in reliable detection of mast cells.

The use of imaging in melanoma, in particular, ultrasound, computerized tomography, magnetic resonance imaging, and positron emission tomography is costly and error prone. Ultrasound at 20 MHz tends to overestimate melanoma Breslow thicknesses.

The existing state of the art for analyzing diseases or other abnormal states is insufficient.

There remains a need for improved methods for analyzing diseases or other abnormal states.

SUMMARY OF THE PRESENT INVENTION

Briefly, the present invention includes a method to quantify biomarkers. The method includes providing a sample comprising a biomarker. The biomarker comprises one or more chemicals that are related to a physiological condition. The method also includes using an X-ray fluorescence spectrometer to perform an X-ray fluorescence analysis on the sample to obtain spectral features derived from the biomarker; and quantifying the X-ray fluorescence signal of the biomarker.

Another aspect of the present invention includes a method to diagnose abnormal conditions. The method includes providing one or more clinical samples. The one or more clinical samples comprise a biomarker. The method further includes using an X-ray fluorescence spectrometer to perform an X-ray fluorescence analysis on at least one of the one or more clinical samples to obtain spectral features derived from at least one biomarker. The method further includes quantifying the X-ray fluorescence signal of the biomarker. The method optionally includes the step of obtaining data concerning the at least one of the one or more clinical samples using at least one other test. The method further optionally includes the step of comparing the spectral features derived from the biomarker to data obtained from the at least one other test. The method yet further optionally includes the step of performing a diagnosis.

Still another aspect of the present invention includes a method to identify one or more abnormal portions of a sample. The method includes providing a clinical sample disposed on or in a sample holder, the clinical sample comprising normal and abnormal portions. The method also includes providing an X-ray fluorescence spectrometer comprising an X-ray excitation source. The method further includes using the X-ray fluorescence spectrometer to perform an X-ray fluorescence analysis on the clinical sample to obtain spectral features derived from at least one biomarker. The method also includes using spectral features derived from the biomarker to determine whether at least one portion of the sample is normal or abnormal. The method optionally includes obtaining multiple X-ray fluorescence analyses wherein the sample is disposed at at least two different angles relative to the excitation source. The method further optionally includes the step of constructing a tomogram.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DETAILED DESCRIPTION

Figure 1:
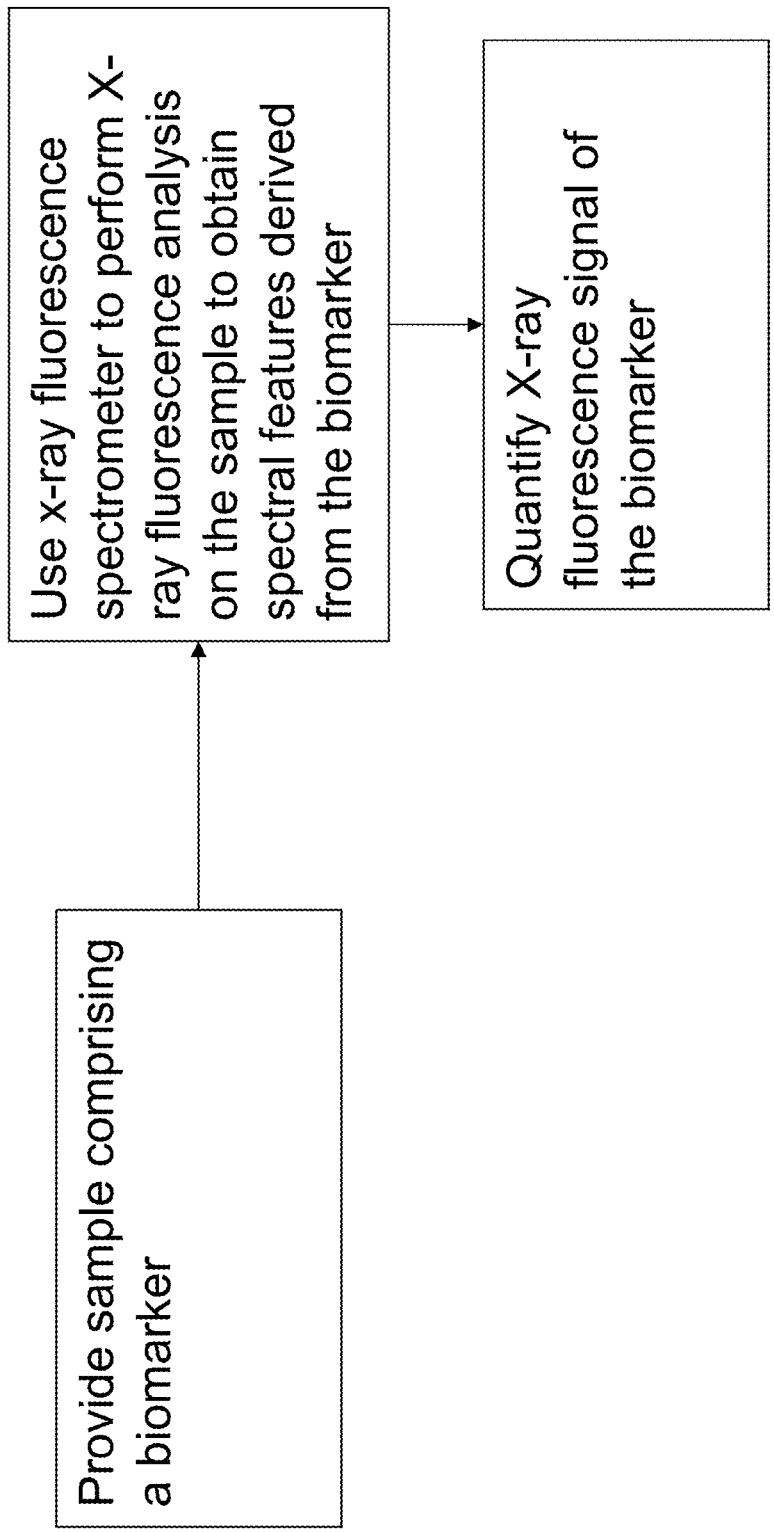
FIG. 1 shows a schematic depiction of one embodiment of the present invention.
Figure 2:
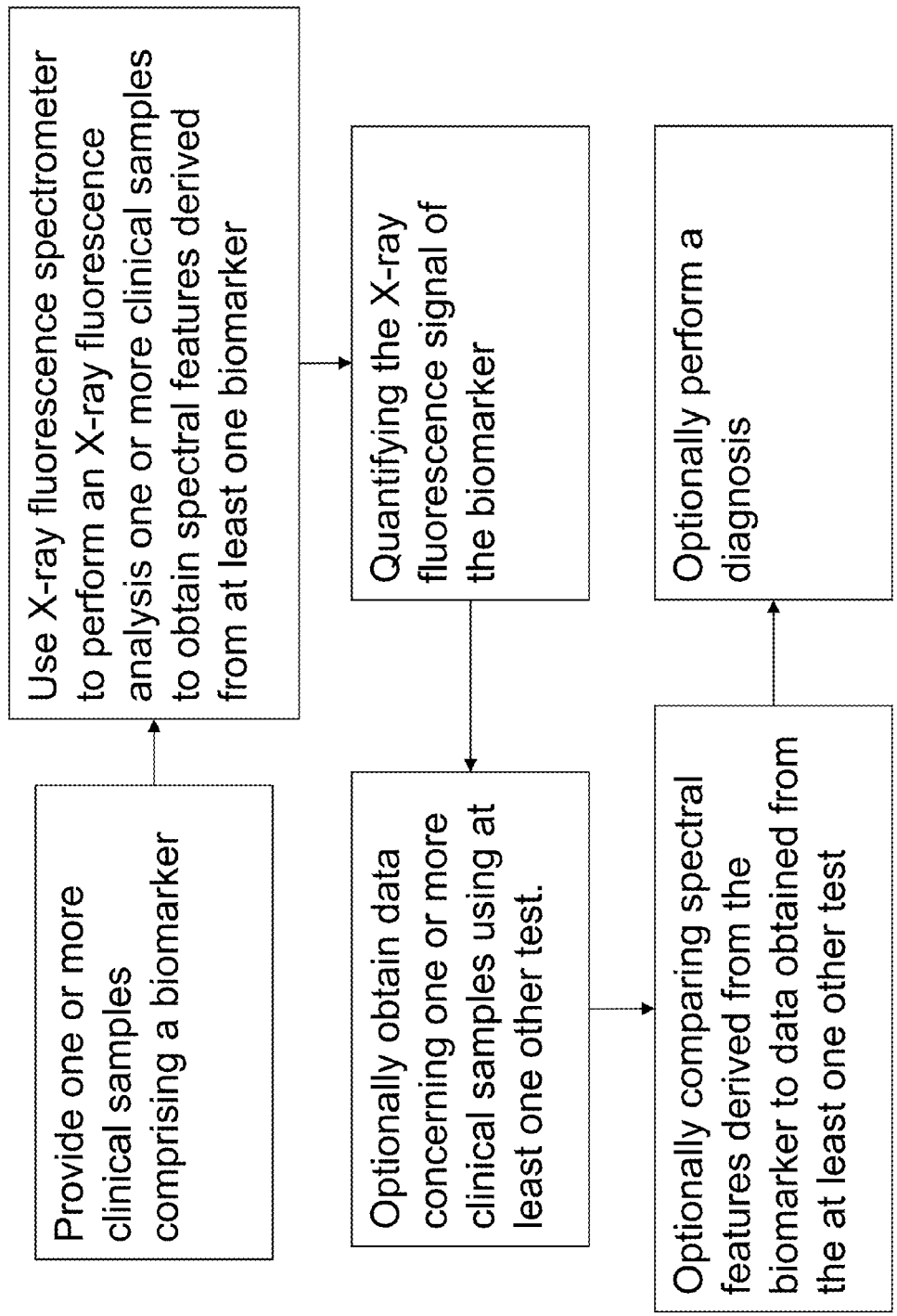
FIG. 2 shows a schematic depiction of another embodiment of the present invention.
Figure 3:
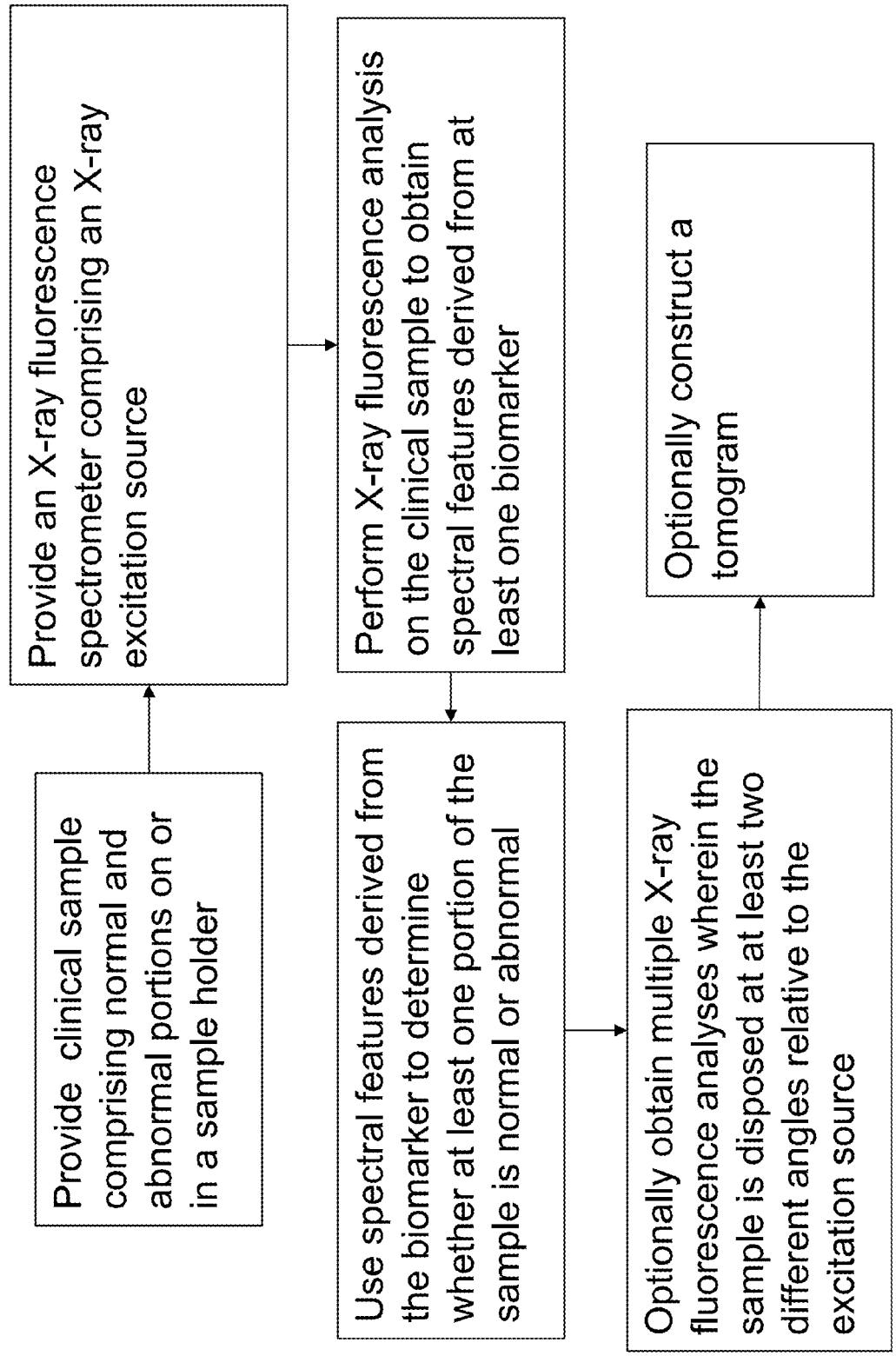
FIG. 3 shows a schematic depiction of yet another embodiment of the present invention.

Briefly, the present invention includes a method to quantify biomarkers. The method includes providing a sample comprising a biomarker. The biomarker comprises one or more chemicals that are related to a physiological condition. The method also includes using an X-ray fluorescence spectrometer to perform an X-ray fluorescence analysis on the sample to obtain spectral features derived from the biomarker; and quantifying the X-ray fluorescence signal of the biomarker.

Another aspect of the present invention includes a method to diagnose abnormal conditions. The method includes providing one or more clinical samples. The one or more clinical samples comprise a biomarker. The method further includes using an X-ray fluorescence spectrometer to perform an X-ray fluorescence analysis on at least one of the one or more clinical samples to obtain spectral features derived from at least one biomarker. The method further includes quantifying the X-ray fluorescence signal of the biomarker. The method optionally includes the step of obtaining data concerning the at least one of the one or more clinical samples using at least one other test. The method further optionally includes the step of comparing the spectral features derived from the biomarker to data obtained from the at least one other test. The method yet further optionally includes the step of performing a diagnosis.

Still another aspect of the present invention includes a method to identify one or more abnormal portions of a sample. The method includes providing a clinical sample disposed on or in a sample holder, the clinical sample comprising normal and abnormal portions. The method also includes providing an X-ray fluorescence spectrometer comprising an X-ray excitation source. The method further includes using the X-ray fluorescence spectrometer to perform an X-ray fluorescence analysis on the clinical sample to obtain spectral features derived from at least one biomarker. The method also includes using spectral features derived from the biomarker to determine whether at least one portion of the sample is normal or abnormal. The method optionally includes obtaining multiple X-ray fluorescence analyses wherein the sample is disposed at at least two different angles relative to the excitation source. The method further optionally includes the step of constructing a tomogram.

The X-ray fluorescence analysis may be conveniently performed using an X-ray fluorescence spectrometer. An X-ray fluorescence spectrometer is an apparatus capable of irradiating a sample with an X-ray beam, detecting the X-ray fluorescence from the sample, and using the X-ray fluorescence to determine which elements are present in the sample and measuring the quantity of these elements. An example of an X-ray fluorescence spectrometer which may be used with the present invention includes the EDAX Eagle XPL energy dispersive X-ray fluorescence spectrometer, equipped with a microfocus X-ray tube, lithium drifted silicon solid-state detector, a sample stage, processing electronics, and vendor supplied operating software, available from the EDAX division of Ametek, 91 McKee Drive Mahwah, N.J. 07430. An example of an X-ray fluorescence spectrometer which may be used with the present invention includes the ZSX Primus, available from Rigaku Americas, 9009 New Trails Drive, The Woodlands, Tex. 77381. The X-ray fluorescence instrument preferably comprises at least one of the following: a monocapillary focusing optic, polycapillary focusing optic, a doubly curved crystal focusing optic, a collimator, a microfocus X-ray tube, a synchrotron X-ray source, a linear accelerator X-ray source, a rhodium X-ray tube, a molybdenum X-ray tube, a chromium X-ray tube, a silver X-ray tube, a palladium X-ray tube, a monochromatic X-ray source, a polychromatic X-ray source, a polarized X-ray source, a confocal X-ray fluorescence spectrometer focusing arrangement, a PIN diode detector, a semiconductor X-ray detector, a germanium or doped germanium X-ray detector, a silicon or doped silicon X-ray detector, a wavelength dispersive X-ray fluorescence spectrometer, an energy dispersive X-ray fluorescence spectrometer, total reflectance X-ray fluorescence spectrometer, and the like. Preferably, the X-ray excitation source emits X-ray having a polychromatic X-ray excitation spectrum, and more preferably the X-ray excitation source emits X-rays having a spectrum with at least two maxima. Excitation with polychromatic X-rays increases the efficiency for exciting more than one chemical element in the sample being analyzed, or for exciting more than one spectral feature in the chemical analyte being analyzed. The X-ray fluorescence spectrometer preferably comprises an X-ray tube. The X-ray tube preferably consumes less than 20 kilowatts of power, and more preferably consumes less than 5 kilowatts of power. The X-ray tube most preferably consumes less than five hundred watts of power. The significance of these power levels is that benchtop equipment may be conveniently shielded against X-ray leakage when the X-ray tube has these power levels. The X-ray fluorescence spectrometer preferably comprises one or more filters disposed between the X-ray excitation source and the sample. The filter or filters serve to attenuate the different energy X-rays in the X-ray excitation beam to different degrees. Filters are useful because they can reduce unwanted X-ray signals from the sample, which often has the effect of dramatically speeding up the X-ray fluorescence analysis. Filters are used to decrease the dead time of the X-ray fluorescence detector. The dead time is preferably less than about 66%, and more preferably less than 50%, and most preferably between 0.5% and 50%. Examples of filters include aluminum, titanium, iron, cellulose, chromium, nickel and rhodium, preferably having a thickness of between 2 microns and 1000 microns. If the X-ray fluorescence analysis is performed on multiple spatial points on the sample, it preferable to perform the X-ray fluorescence analysis at a rate of at least one pixel per five seconds. The X-ray excitation beam preferably has a spatial cross section of less than about 500 microns, and more preferably less than 100 microns, for X-rays having an energy of 5,000 electron volts at the point at which the excitation beam impinges on the sample.

Figure 8:
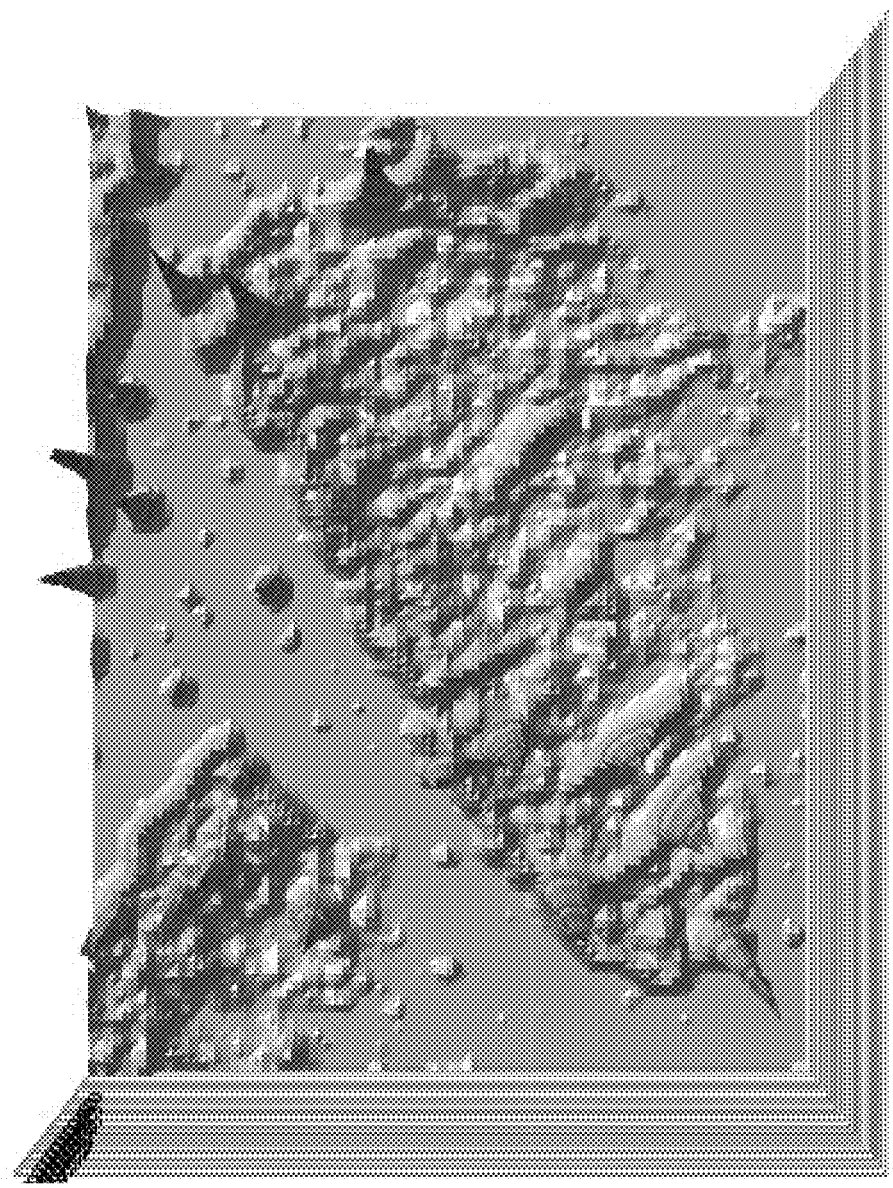
FIG. 8 shows a map of the sulfur intensity of the sample shown in FIG. 7, as measured by X-ray fluorescence spectrometry, as described in Example 2.
Figure 9:
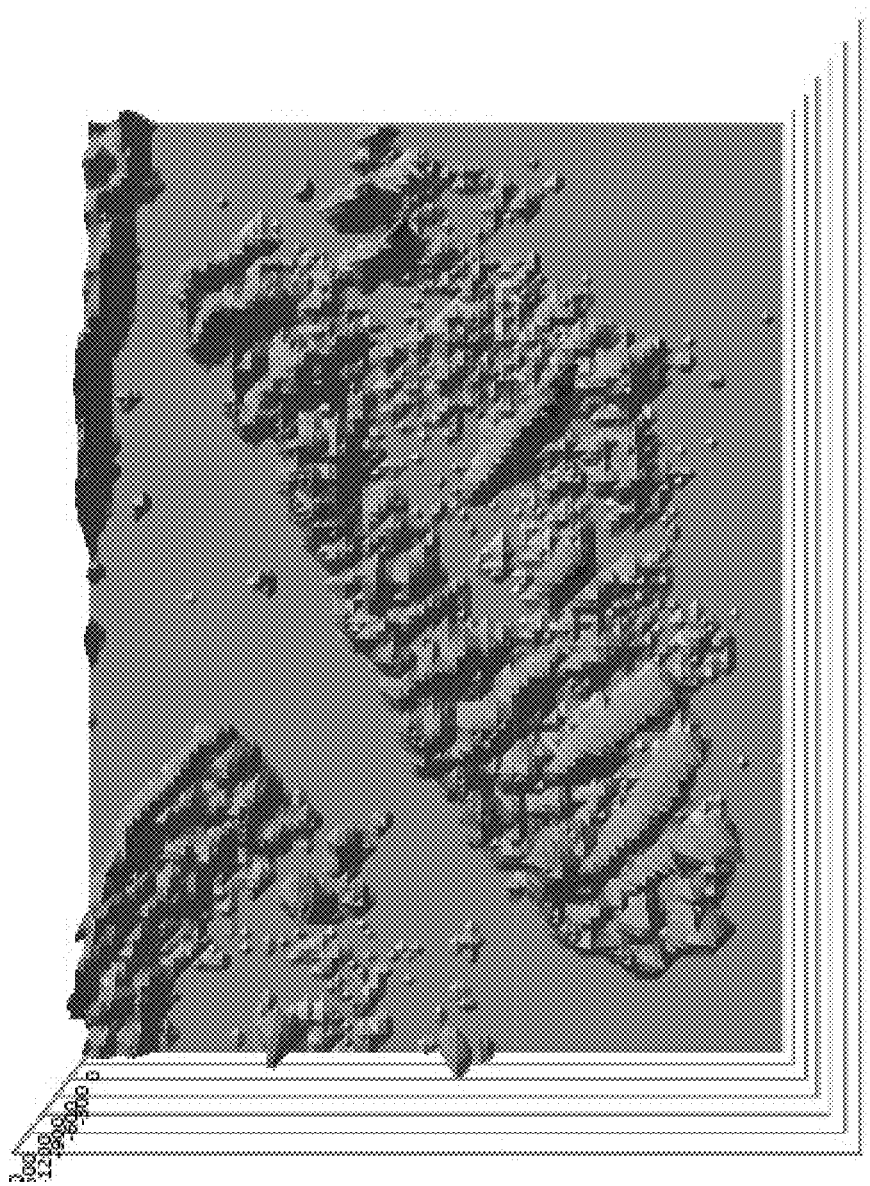
FIG. 9 shows a map of the phosphorus intensity of the sample shown in FIG. 7, as measured by X-ray fluorescence spectrometry, as described in Example 2.
Figure 10:
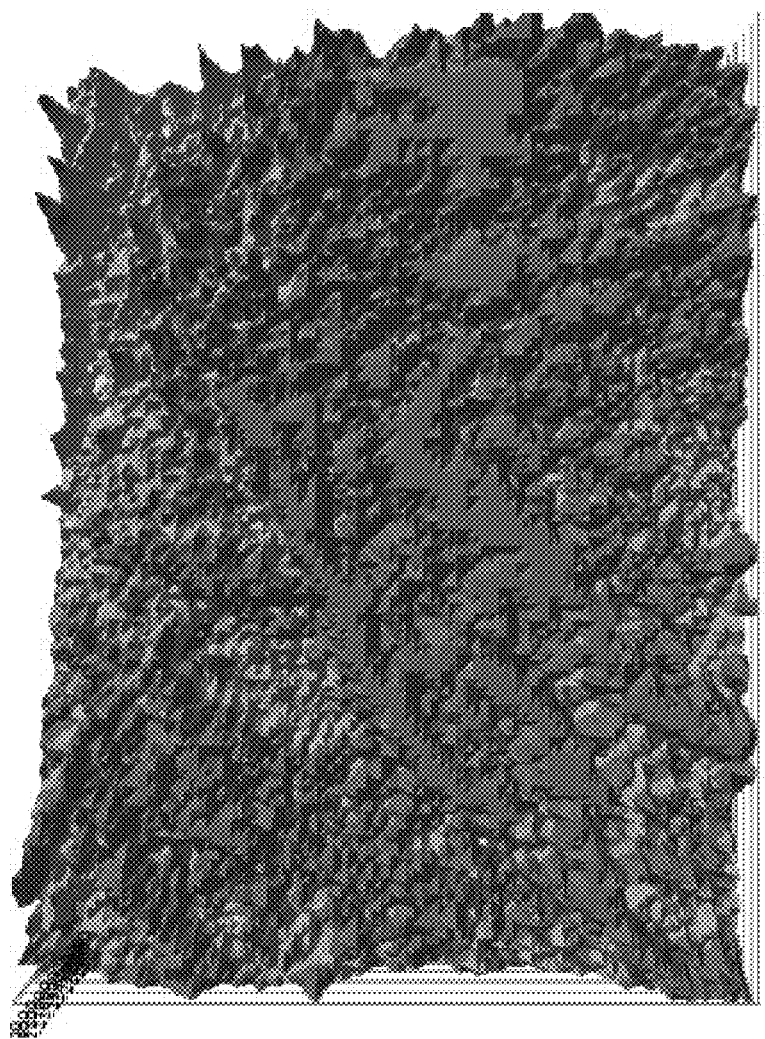
FIG. 10 shows a map of the rhodium scatter intensity of the sample shown in FIG. 7, as measured by X-ray fluorescence spectrometry, as described in Example 2.

The sample is preferably measured using X-ray fluorescence spectrometry at multiple emission wavelengths, which allows multiple elements to be measured simultaneously. The X-ray fluorescence spectrometer performs x-ray fluorescence spectrometry. X-ray fluorescence spectrometry is used to identify chemical elements by the energy or energies of signals in the x-ray fluorescence spectrogram. X-ray fluorescence spectrometry is used to quantify chemical elements by the amplitude of signals, also referred to as peaks, in the x-ray fluorescence spectrogram. For example, FIG. 4, FIG. 5, FIG. 6, FIG. 11, FIG. 12, and FIG. 15 show examples of X-ray fluorescence spectrograms with peaks, with the peaks labeled with the chemical elements that produce the x-ray fluorescence signals at the peaks. The area under the peaks is proportional to the quantity of the element that produces that peak, corrected for the sensitivity for that element for the x-ray fluorescence spectrometer being used. The area under each peak is typically derived from counting the x-rays fluoresced or scattered from the sample having energies associated with the element being measured. The x-ray fluorescence spectrometer typically presents the quantity of each element measured as a spreadsheet or database with numerical data. The x-ray fluorescence spectrometer may be calibrated so that the amount of an element that produces a peak may be correlated to the area under that peak. It is not necessary to generate a spectrogram and measure the area under each peak. X-rays may also be measured as a count rate, typically counts of x-rays having the appropriate energies per second. The amount of x-rays at appropriate energies may also be counted. Mathematical manipulations of the data are typically performed, for example to remove background and noise and to allow statistics to be determined and to allow algorithms to be used for diagnostic, prognostic, response, and/or health status biomarkers. For example, means, ratios, and/or principal component analysis may be used to differentiate signals and noise and background. FIG. 8 shows a map constructed by plotting the intensity of the sulfur signals from an x-ray spectrogram obtained from a tissue sample; the contour lines and colors in FIG. 8 are derived from the intensity of the sulfur peak in each x-ray fluorescence spectrogram. The x and y coordinates in FIG. 8 are derived from the x and y coordinates of the measured tissue sample. FIG. 9 shows a map constructed by plotting the intensity of the phosphorus signals from an x-ray spectrogram obtained from a tissue sample; the contour lines and colors in FIG. 9 are derived from the intensity of the phosphorus peak in each x-ray fluorescence spectrogram. The x and y coordinates in FIG. 9 are derived from the x and y coordinates of the measured tissue sample. FIG. 10 shows a map constructed by plotting the intensity of the rhodium signals from an x-ray spectrogram obtained from a tissue sample; the contour lines and colors in FIG. 10 are derived from the intensity of the rhodium peak in each x-ray fluorescence spectrogram. The x and y coordinates in FIG. 10 are derived from the x and y coordinates of the measured tissue sample. Biomarkers are preferably quantified by identifying and quantifying chemical elements in a sample that correlate with a health condition. For example, Example 1 describes a biomarker for thimerosal exposure, which is quantified by the mercury x-ray fluorescence signals as well as other x-ray fluorescence signals in FIG. 5 and the associated numerical data.

The sample should comprise one or more biomarkers. For the present invention, biomarkers are defined as portions of a sample that indicate a physiological state or process. For example, Example 1 describes a biomarker for thimerosal exposure. Example 2 describes biomarkers for melanomic and amelanomic tissue. A biomarker used with the present invention should preferably give rise to an x-ray fluorescence signal that is different from the x-ray fluorescence signal of a sample that does not contain the biomarker. For example, a biomarker of an abnormal state preferably has a different empirical formula from a biomarker for a normal state. Examples of biomarkers that may be used with the present invention include biomarkers that allow or assist in the diagnosis, prognosis, or staging of an abnormal condition and/or assess health status and/or response to therapy. Preferably the biomarker comprises a chemical element having an atomic number greater than 19, and most preferably the biomarker is related to a disease that is associated with a different level of metal homeostatis than is found in healthy patients. Biomarkers used in the present invention may be used with additional panels of biomarkers, such as algorithms used for cancer prognosis such as Breslow depths.

The sample is preferably deposited or mounted onto a sample holder, or into a sample holder. Solid samples are preferably disposed on a slide or a film or a well plate. Liquid samples are preferably disposed on a slide or a film, or else may be placed in a container such as a cup or a well. The sample holder may be used to concentrate the sample to increase X-ray fluorescence signals. The sample holder is preferably substantially free of at least one of the elements selected from the list comprising sulfur, phosphorus, silicon, potassium, calcium, manganese, iron, cobalt, nickel, copper, zinc, arsenic, rhodium, molybdenum, chromium, selenium, bromine, silver, cadmium, platinum, gold, mercury, lead, gadolinium, dysprosium, terbium, europium, strontium, cesium, barium, and iodine; these elements are commonly present in samples to be measured, or else X-rays derived from these elements are commonly present in measurements. Examples of suitable materials for the deposition substrate include Porvair #229302, Porvair #229112, Porvair # 229058, Porvair # 229304, and Porvair #229301, all of which are available from Porvair plc, Brampton House, 50 Bergen Way, King's Lynn, Norfolk PE30 2JG, U.K.), aluminum foils (examples: Microseal 'F' Foil from Bio-Rad Laboratories, 1000 Alfred Nobel Drive, Hercules, Calif. 94547). Other materials that may be used for the deposition substrate include: polyvinylidene difluoride, polyvinylidene fluoride, cellulose, filter paper, polystyrene, agarose, Super-Thin Polyester Surface-Protection Tape, Chemical-Resistant Surlyn Surface-Protection Tape, Abrasion-Resistant Polyurethane Surface-Protection Tape, Heat-Resistant Kapton Tape with Silicone Adhesive or with Acrylic Adhesive, UV-Resistant Polyethylene Surface-Protection Tape, Clean-Release Polyethylene Surface-Protection Tape, Low-Static Polyimide Tape, all available from McMaster-Carr, 6100 Fulton Industrial Blvd., Atlanta, Ga. 30336-2852. Other materials which may be used for the deposition substrate include polypropylene, available from Lebow Company, 5960 Mandarin Ave., Goleta, Calif. 93117 U.S.A. Other substrates that are conveniently used for the deposition substrate include AP1, AP3, ProLINE Series 10, ProLINE Series 20, DuraBeryllium substrates from Moxtek, 452 West 1260 North, Orem, Utah 84057. Other materials which may be used for the deposition substrate include Ultralene®, mylar, polycarbonate, prolene, and kapton, available from SPEX CertiPrep Ltd, 2 Dalston Gardens, Stanmore, Middlesex HA7 1BQ, ENGLAND. Other materials that may be used as the deposition substrate include Hostaphan®, polyester, and Etnom® available from Chemplex Industries, Inc., 2820 SW 42nd Avenue, Palm City, Fla. 34990-5573 USA. Another material that may be conveniently used is Zone Free Film Part ZAF-PE-50, available from Excel Scientific, 18350 George Blvd, Victorville, Calif., 92394. Other useful substrates are glass and silicon. This list is not exhaustive, and other materials may be used as the deposition substrate. The deposition substrate is also preferably substantially free of elements which have X-ray fluorescence emission peaks having energies of between 1.9 KeV and 3 KeV, because these peaks tend to interfere with the signals of most interest to biochemical and biological applications. Elements which have X-Ray Fluorescence emission peaks having energies of between 1.9 KeV and 3 KeV are: osmium, yttrium, iridium, phosphorus, zirconium, platinum, gold, niobium, mercury, thallium, molybdenum, sulfur, lead, bismuth, technetium, ruthenium, chlorine, rhodium, palladium, argon, silver, and thorium. If an X-ray fluorescence spectrometer is used which uses an X-ray detector which comprises silicon, then the deposition substrate is also preferably free of elements which have X-ray fluorescence escape peaks (i.e. X-ray fluorescence emission peaks minus 1.74 KeV) having energies of between 1.9 KeV and 3 KeV, because these escape peaks tend to interfere with the signals of most interest for biochemical and biological applications. Elements which have X-Ray Fluorescence escape peaks having energies of between 1.9 KeV and 3 KeV are: calcium, tellurium, iodine, scandium, xenon, cesium, barium, titanium, and lanthanum. "Substantially free" is defined herein as being less than about 4% by weight. The deposition substrate may have additional chemical elements, which may be used for measuring the thickness of the sample. If wavelength dispersive X-ray fluorescence is used, then the elemental purity of the deposition substrate is not as important; in this case, the film should be substantially free of the element or elements which are being used to quantify the sample. The deposition substrate may be treated to increase protein adhesion; a non-inclusive list of treatments includes treating the deposition substrate with oxygen or nitrogen plasma or with poly-lysine. The sample holder also preferably comprises at least one element that is not present in the sample at concentrations above one weight percent in any pixel of the sample.

Many samples, including clinical samples, are washed or otherwise exposed to a solution that serves to buffer the pH of the sample, buffer the redox state of the sample, preserve the sample, fix the sample, sterilize the sample or otherwise render the sample safe or prepared for reading. Many of these solutions contain elements which might interfere with the measurement of the sample. The solution should preferably be free of at least one chemical element having an atomic number of greater than four, where that chemical element is present in the sample. The solution should more preferably be free of at least one chemical element having an atomic number of greater than eight, where that chemical element is present in the sample. The solution should preferably be free of at least one of the following chemicals or functional groups: dimethylsulfoxide, thiols, sulfate anion, sulfonate anions, chloride anion, bromide anion, fluoride anion, iodide anion, perchlorate anion, phosphate anion, and phosphonate anions. The solution preferably comprises one or more of the following chemical or functional groups: amine, imine, nitrate anion, nitrite anion, ammonium cation, acetate anion, carboxylate anion, conjugate bases of carboxylic acids, carbonate anion, formalin, formaldehyde, ethanol, 2-propanol, and iminium cation; these chemicals offer the correct chemical properties with minimal X-ray fluorescence interference. The solution is most preferably substantially free of at least one element selected from the list of phosphorus and sulfur.

If the sample holder comprises at least one element which is not present in the sample, then an X-ray fluorescence signal from the sample holder may be compared, for example, by obtaining a ratio, to an X-ray fluorescence signal from the sample. For example, if the sample holder comprises silicon and the sample comprises sulfur, then the ratio of sulfur to silicon may be used to estimate the thickness of the sample.

The sample is preferably a biological or environmental specimen. Examples of biological specimens are tissue samples, such as adipose cells, adipose tissue, aneuploid regions, apoptotic regions, arthropods, bacteria, biological fluids, biopsy samples, buffy coat containing oligonucleotides, cell cycle related regions, cells, cerebrospinal fluid, differentiated regions, dried biospecimens, erythrocytes, fresh biospecimens, fungi, hemolysate, immortalized cell lines, infectious agents, lymph nodes, lyophilized biospecimens, membranes, metastatic sites, microenvironment regions, microtome cut biospecimens, mitotic regions, nucleotides, organelles, organs, paraffin fixed biospecimens, plasma, primary cell cultures, prions, proteins, protozoa, serum, snap frozen biospecimens, stem cells, stromal tissue, subcellular fractionates, tissue homogenate, tissue microarrays, tissues, tissue samples showing infiltration beyond surgical margins, urine, viruses, whole blood, and the like. The sample may comprise fractionated specimens; for example, the sample may be one or more biological polymers such as proteins or nucleic acids, amino acids, peptides, polymers comprising amino acids, oligomers comprising amino acids, nucleotides, polymers comprising nucleotides, and oligomers comprising nucleotides. Samples may also be materials emitted or excreted from the body, such as ear wax, urine, feces, breath, saliva, sweat, and the like. More preferably, the sample comprises a disease related tissue such as a tumor specimen, such as a melanoma-containing sample.

The sample may be stained using a chemical element that is not commonly found in the sample, or by using a chemical comprising a chemical element that is not commonly found in the sample. This X-ray fluorescence staining is preferably performed using a chemical element having an atomic number of 19 or greater or chemical comprising a chemical element having an atomic number of 19 or greater. It is especially convenient to use a drug that comprises one or more chemical elements having an atomic number of 19 or greater to stain a sample. The X-ray fluorescence analysis is quantitative, so the amount of stain and sample may be determined and a ratio may be determined Multiple assays, for example, using two different stains, where one of the stains comprises one of the chemical elements having an atomic number of 19 or greater and the other stain comprises a different chemical element having an atomic number of 19 or greater may be performed and analyzed by X-ray fluorescence spectrometry to identify regions of the sample that differ in chemical or biological makeup. Alternatively, multiple assays using two different stains, where one of the stains comprises one of the chemical elements having an atomic number of 19 or greater and the other stain does not comprise that chemical element having an atomic number of 19 or greater may be performed and analyzed by X-ray fluorescence spectrometry and a second analytical technique to identify regions of the sample that differ in chemical or biological makeup.

Samples may be fractionated. If a sample is fractionated, it is often convenient to homogenize the sample before fractionating. Samples may be homogenized by physical (e.g., cold denaturation or heating), mechanical (e.g., cutting, grinding, shearing, beating, shocking, sonication, blending), chemical (e.g., pH or chemical denaturation), or enzymatic (e.g., proteases) means, or a combination of these methods. The sample may be fractionated, separated or depleted, with analysis of fractions containing analytes for detection of the presence, absence, or ratios of target analytes. Examples of fractionation techniques include centrifugation; mechanical separation; chemical separation; enzymatic separation; condensation; chromatographic methods such as ion exchange chromatography, affinity chromatography, immunochromatography, thin layer chromatography, gel filtration chromatography, high performance liquid chromatography; gel electrophoresis; isoelectric focusing; 2D electrophoresis; precipitation; density gradient fractionation; and immobilization of analytes to solid formats such as beads, membranes, arrays, microarrays, spin plate, or well plates before X-ray fluorescence measurements.

The sample may be analyzed by X-ray fluorescence mapping. Mapping comprises obtaining multiple X-ray fluorescence measurements of one or more elements, at multiple locations on the sample. The sample may be mapped while it is oriented in at least two different angles relative to the X-ray excitation beam. The angle at which the sample is oriented to the X-ray beam may be conveniently adjusted, for example, by tilting the stage or placing a shim underneath the sample or sample holder, or using a sample mount capable of rotating in one or more axes. If the sample is measured in this manner, the X-ray fluorescence data may be displayed to appear three dimensional, for example, by projecting the images from each location in a different color or with imaged displayed with different polarizations. The image may then viewed with glasses having different polarized lenses, different colored lenses, as cross-eye or wall-eye stereo image pairs, or using other standard three dimensional imaging techniques. The image may also be reconstructed using computer tomography to construct a three dimensional image or a tomogram.

Additional tests may be performed on the sample and the results of these tests may be compared to the features obtained through the X-ray fluorescence analysis. Other clinical tests that may be used in the present invention include research or clinical methods used for identifying, diagnosing, prognosing, staging of disease and methods used to assess response to therapies. Examples of these methods include analysis using antibodies, angiogenesis scanning, biochemical assays, biomarker panels, Breslow Depth analysis, cancer staging, Clark level analysis, clinical exam, clinical pathology, computerized tomography, darkfield miscroscopy, density analysis, electron microscopy, enzymatic or colorimetric assays, flow cytometry, fluorescence in situ hybridization, genetic analysis, genotyping, hematoxylin and eosin staining (HE staining), histological assays, magnetic resonance angiography, immunoassays, immunohistochemistry, infrared microscopy, infrared spectroscopy, karyotyping, magnetic resonance imaging, mass spectroscopy, micronutrient and macronutrient status, monochromatic X-ray fluorescence analysis, nuclear magnetic resonance spectroscopy, optical microscopy, phase contrast microscopy, phenotyping, positron emission tomography, single photon emission computed tomography, staining, synchrotron X-ray fluorescence, ultraviolet spectroscopy, ultraviolet microscopy, visible light microscopy with or without stains and histological markers, X-ray absorbance, X-ray scatter, and fluorescence microscopy wherein fluorescent signals are intrinsic or arise from staining, and the like.

If multiple clinical samples are analyzed by X-ray fluorescence and a second test, then preferably the clinical samples are derived from the same patient. More preferably, the samples are obtained from at most six inches apart from each other. Most preferably, the clinical are sufficiently proximal in space or time of collection such that at least two of the clinical samples comprise the feature that is being assessed.

X-ray fluorescence data and data resulting from additional tests may be conveniently analyzed using mathematical manipulations to identify sample regions with differing compositions. Simple methods include generating and displaying images of the sum, difference, product or quotient of data from X-ray fluorescence and additional tests and analyses described above. In addition, multiple data sets from X-ray fluorescence and additional tests may be analyzed together using multivariable statistical approaches, including component analysis, correspondence analysis, covariation analysis, dimensional reduction, factor analysis, independent component analysis, K-means clustering, neural network analyses, nonlinear dimensional reduction, principle component analysis, targeted vector rotation, and the like. This list is not exhaustive and other methods may be employed. Analyses are conveniently carried out using mathematical and statistical software packages to generate statistical results and images of resultant data, including, Matlab (MathWorks, Natick Mass. 01760), IDL (ITT Visual Information Solutions, Boulder Colo. 80301), SPSS (International Business Machines Corp. Armonk, N.Y., 10504.) Results may be visualized as tabulated values, or more conveniently as either two-dimensional images with false color or monotone color scales to represent data or as three-dimensional surface plots displaying data as peak heights. For comparison of results for multiple data sources or analyses, multiple data sets may be combined using multiple colors to compare, most conveniently using red, green and blue.

The X-ray fluorescence data may be used to diagnose a sample. The X-ray fluorescence analysis may be used to diagnose chromium exposure, as described in Example 3. Regions of high phosphorus signals may be used to diagnose aneuploidy. When a rhodium X-ray tube is use, regions of high rhodium scatter signals may be used to identify adipose tissue and to diagnose obesity. Changes in ratios between multiple elements can be used to diagnose conditions such as micronutrient deficiencies and diseases that affect metabolism of one or more specific nutrients; examples of such diseases are Wilson's disease and Menkes disease and anemia. The diagnosis is conveniently performed by comparing the X-ray fluorescence signal or signals from healthy samples and abnormal samples to the sample being diagnosed.

The X-ray fluorescence analysis may be used to determine normal or abnormal portions of the sample, or boundaries of abnormal and normal tissue regions. The sample may be mapped using a single elemental signal in the X-ray fluorescence measurement. However, preferably, more than one single elemental signal in the X-ray fluorescence measurement is used. Regions of high phosphorus signals, which are conveniently measured by the phosphorus K-alpha X-ray fluorescence peak, are associated with post-translationally modified proteins, nucleotides, or aneuploidy; cells that undergo carcinogenesis often show abnormal numbers of chromosomes called aneuploidy. Regions of high scatter signals, which are conveniently measured by the rhodium L-alpha X-ray fluorescence peak when using a rhodium X-ray tube for the excitation source (as shown in Example 2), are associated with adipose tissue or fat cells; other convenient signals are the chromium K-alpha line when a chromium X-ray tube is used, the molybdenum L-alpha line when a molybdenum X-ray tube is used. The density of a sample may be conveniently measured, for example, if the sample holder comprises at least one element that is not present in the sample. In this case, the attenuation of the X-ray fluorescence signal derived from elements in the sample holder that are not present in the sample may be correlated to the density of the sample. Examples of normal and abnormal portions of samples include the border between normal and abnormal, i.e. where a first pixel shows normal tissue and the next pixel shows abnormal tissue. Other boundaries can include perinormal regions, samples that include metals or other elements such as strontium or mercury, metastasized cells, dead cells, apoptotic cells, diseased cells or tissues, peritumor environments, stroma environments, disease microenvironments and precursor regions. Another example of abnormal sample includes gadolinium from a magnetic resonance imaging contrast agent, such as gadopentic acid, that is not in the desired tissue. Yet another example of abnormal sample includes platinum from a platinum-containing chemotherapeutic agent such as cis-platin, that is not in the tumor. Yet another example includes finding lead or mercury in sample because this element is harmful to health and may be involved in neurodegeneration and other diseases such as autism spectrum disorder.

The embodiments of the present invention may be understood from the following examples.

EXAMPLE 1

Figure 4:
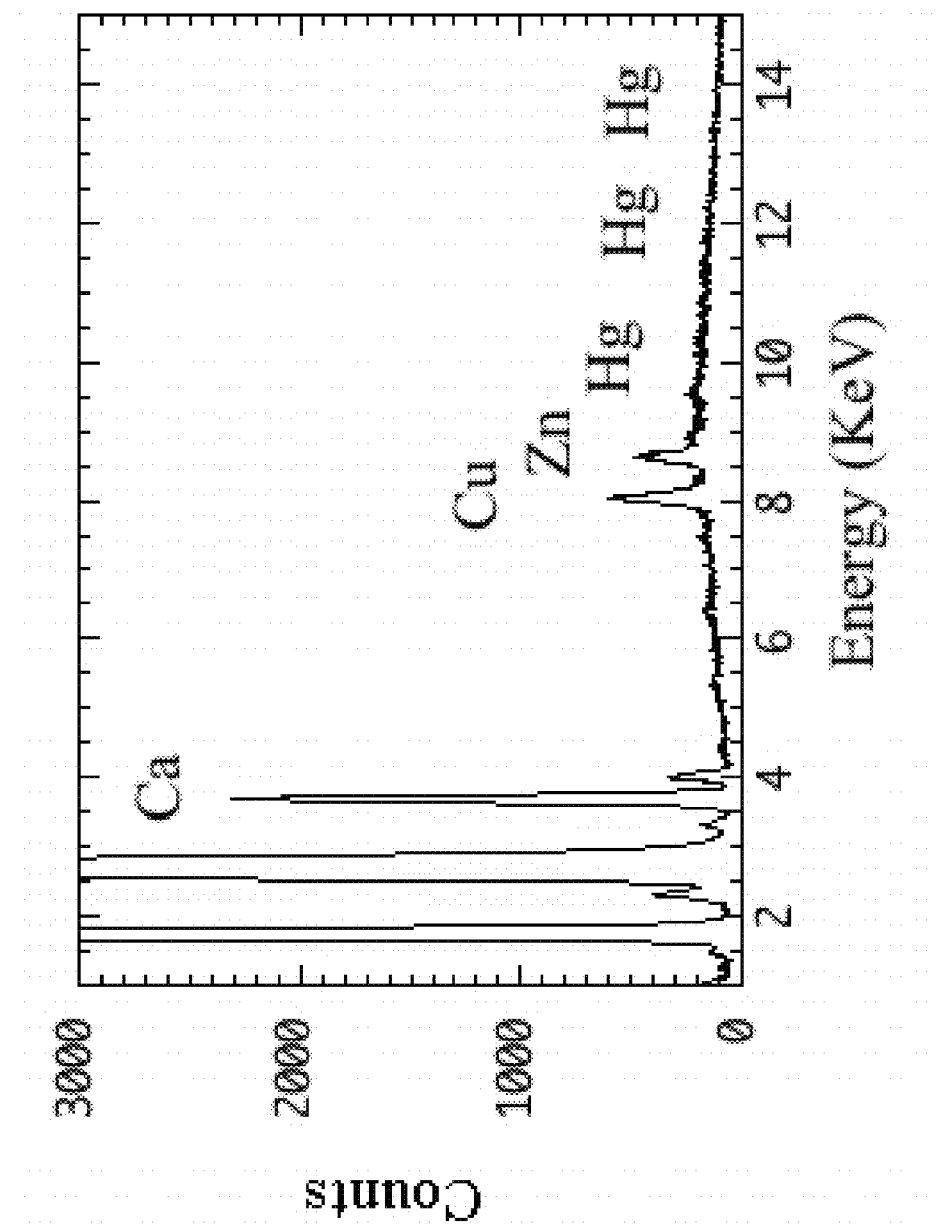
FIG. 4 shows an X-ray fluorescence spectrum of bovine serum albumin as described in Example 1.
Figure 5:
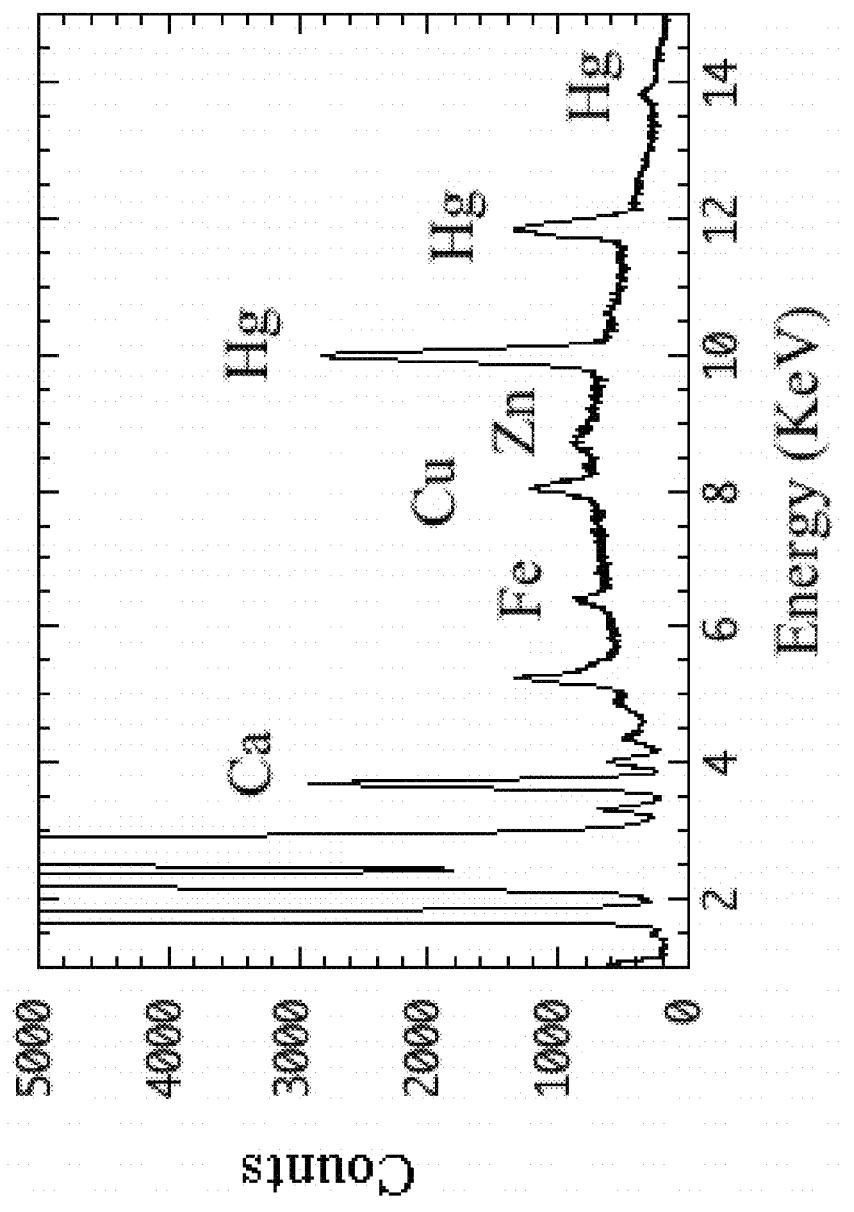
FIG. 5 shows an X-ray fluorescence spectrum of bovine serum albumin that was exposed to thimerosal, as described in Example 1.
Figure 6:
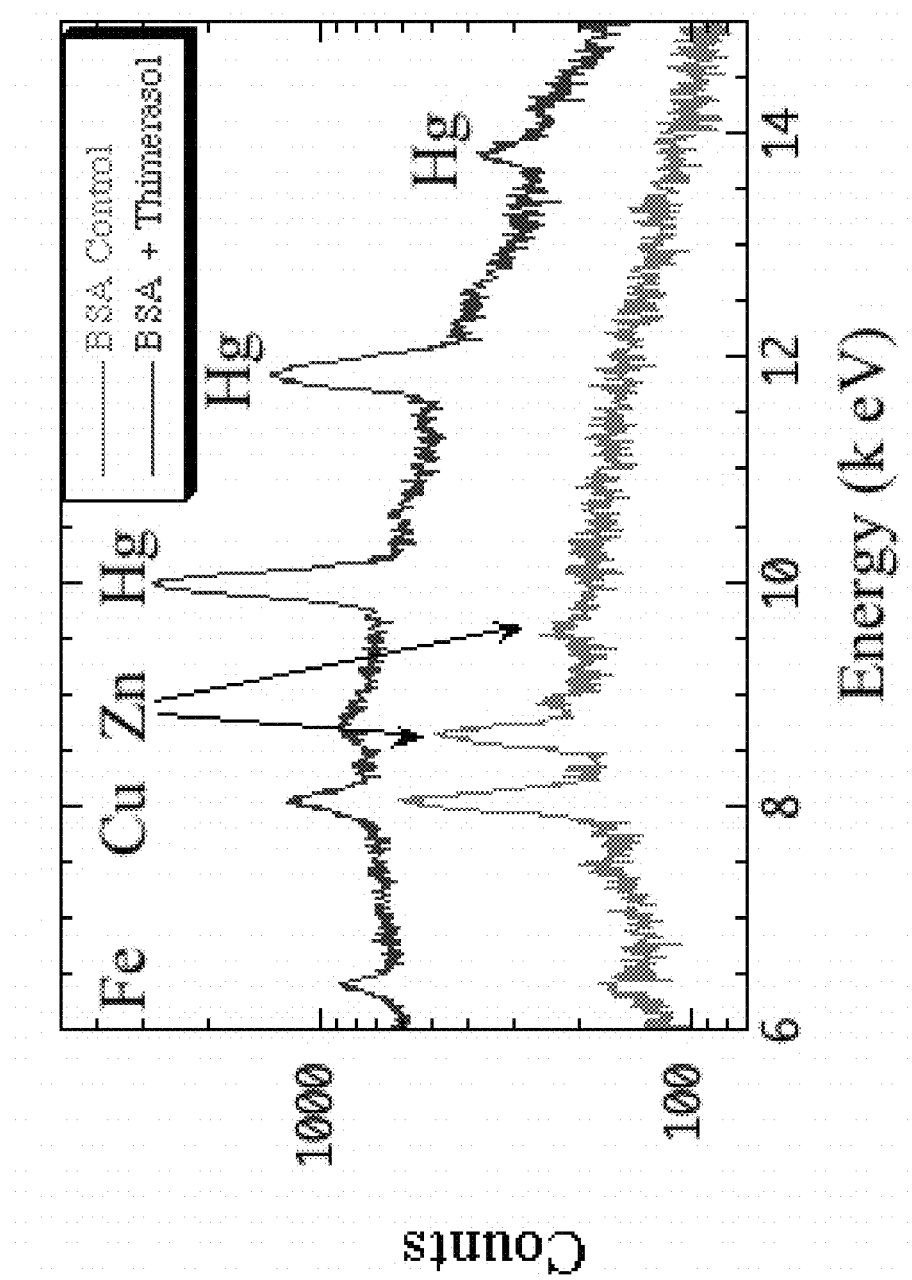
FIG. 6 shows an overlay of an X-ray fluorescence spectrum of bovine serum albumin and an X-ray fluorescence spectrum of bovine serum albumin that was exposed to thimerosal, as described in Example 1.

A solution of bovine serum albumin (150 nanomolar in pH 7.5 tris(hydroxymethl)amine-hydrochloric acid buffer) was exposed to thimerosal. FIG. 4 shows the X-ray fluorescence spectra of bovine serum albumin that was not exposed to thimerosal. FIG. 5 shows the X-ray fluorescence spectrum of bovine serum albumin that was exposed to 9 millimolar thimerosal. FIG. 6 shows an expanded the X-ray fluorescence spectra of bovine serum albumin that was not exposed to thimerosal (bottom spectrum) and the X-ray fluorescence spectrum of bovine serum albumin that was exposed to 9 millimolar thimerosal (top spectrum). As can be seen in FIGS. 4-6, the bovine mercury appears to displace a portion of the copper and zinc from the bovine serum albumin. The biomarkers for thimerosal exposure to bovine serum albumin are increased mercury X-ray fluorescence signals, and decreased copper and zinc X-ray fluorescence signals. As an example of x-ray fluorescence data, the following is a list of elements and the net counts for the spectrum shown in FIG. 5: P, 829.8 counts above background; S, 17706.6 counts above background; Cl, 1723.2 counts above background; Rh, 38125.2 counts above background; K, 198 counts above background; Ca, 232.8 counts above background; Mn, 228 counts above background; Fe, 301.8 counts above background; Co, 199.8 counts above background; Ni, 283.8 counts above background; Cu, 343.8 counts above background; Zn, 349.2 counts above background; Hg, 760.2 counts above background; As, 193.2 counts above background; Se, 193.8 counts above background; Br, 0 counts above background; Zr, 364.2 counts above background.

EXAMPLE 2

Figure 7:
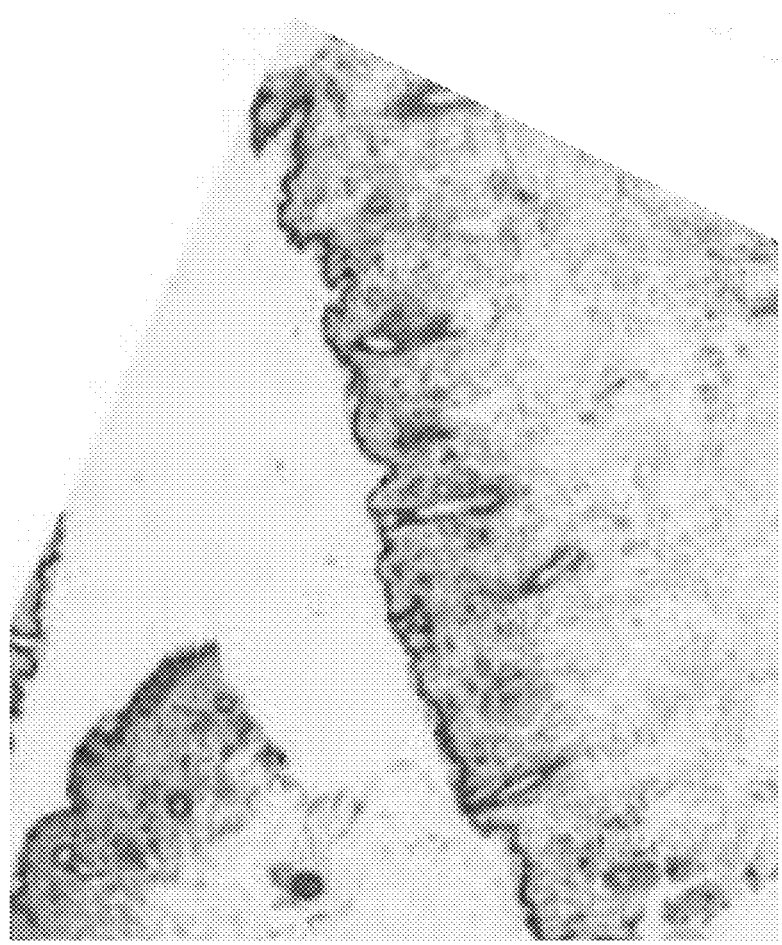
FIG. 7 shows an H&E stained tissue sample comprising regions of melanoma and regions that are amelanocytic, as described in Example 2.

A human tissue sample comprising melanoma and amelanomic regions was analyzed to determine element content using X-ray fluorescence. A 12 millimeter by 7.4 millimeter region was mapped with 0.1 millimeter spatial resolution using a 0.1 millimeter polycapillary X-ray focusing optic, a rhodium X-ray tube for polychromatic X-ray excitation, and silicon drift detector energy dispersive X-ray detector. Elements quantified include phosphorus, sulfur, chlorine, potassium, calcium, iodine, titanium, chromium, manganese, iron, nickel, copper, zinc, platinum, mercury, arsenic, lead, selenium, cadmium, and tin. Images were reconstructed as three dimensional plots which represent element concentration in both color and peak height. FIG. 7 shows an optical micrograph of the H&E stained sample. FIG. 8 shows images for the sulfur signal intensity. FIG. 9 shows images for the phosphorus signal intensity. FIG. 10 shows images for the elastic scatter of the rhodium L-line. Elastic Rh scatter correlates inversely with tissue density, while P and S signals correlate positively with tissue density. Abnormal areas are characterized by altered P to S ratios.

EXAMPLE 3

Figure 11:
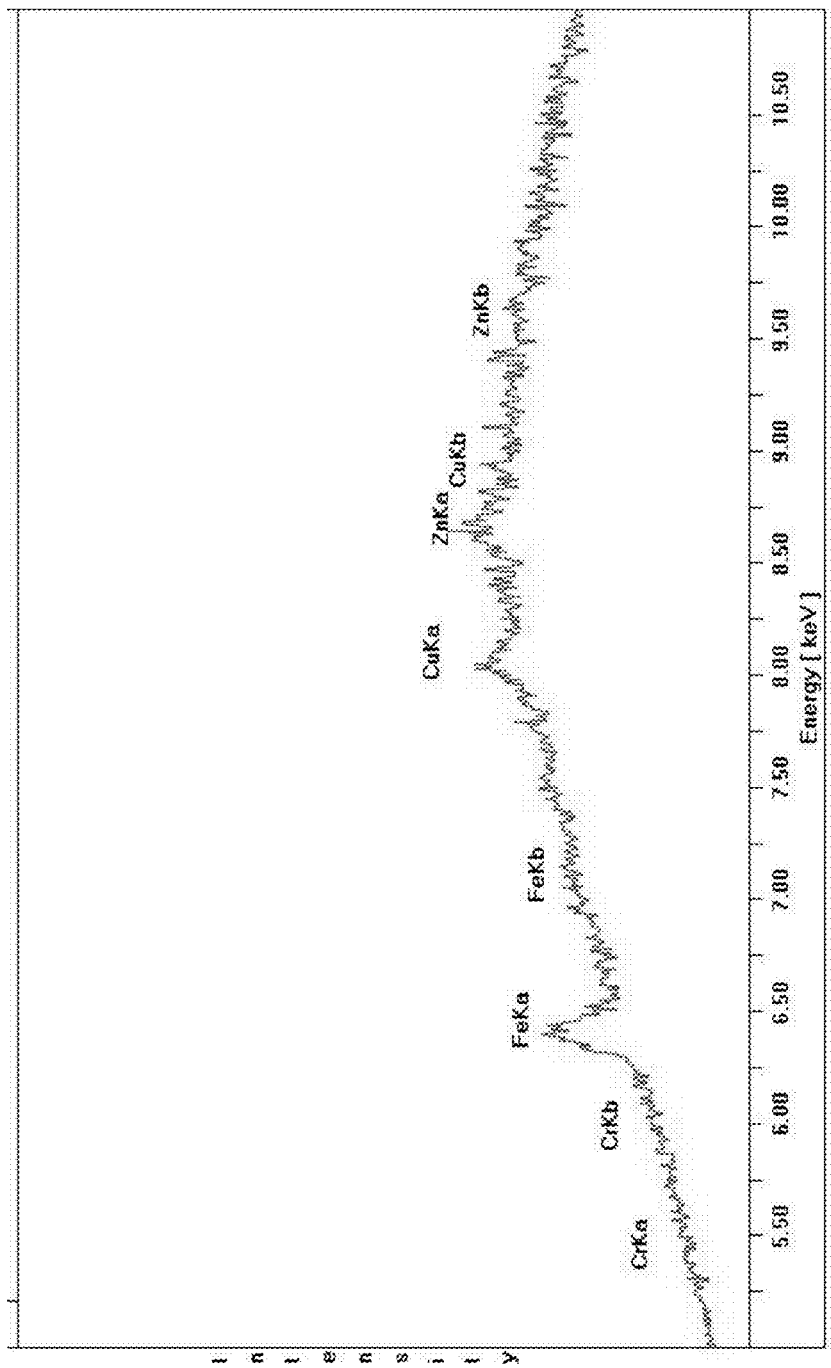
FIG. 11 shows elemental spectrum of control cells not exposed to chromium, as described in Example 3.
Figure 12:
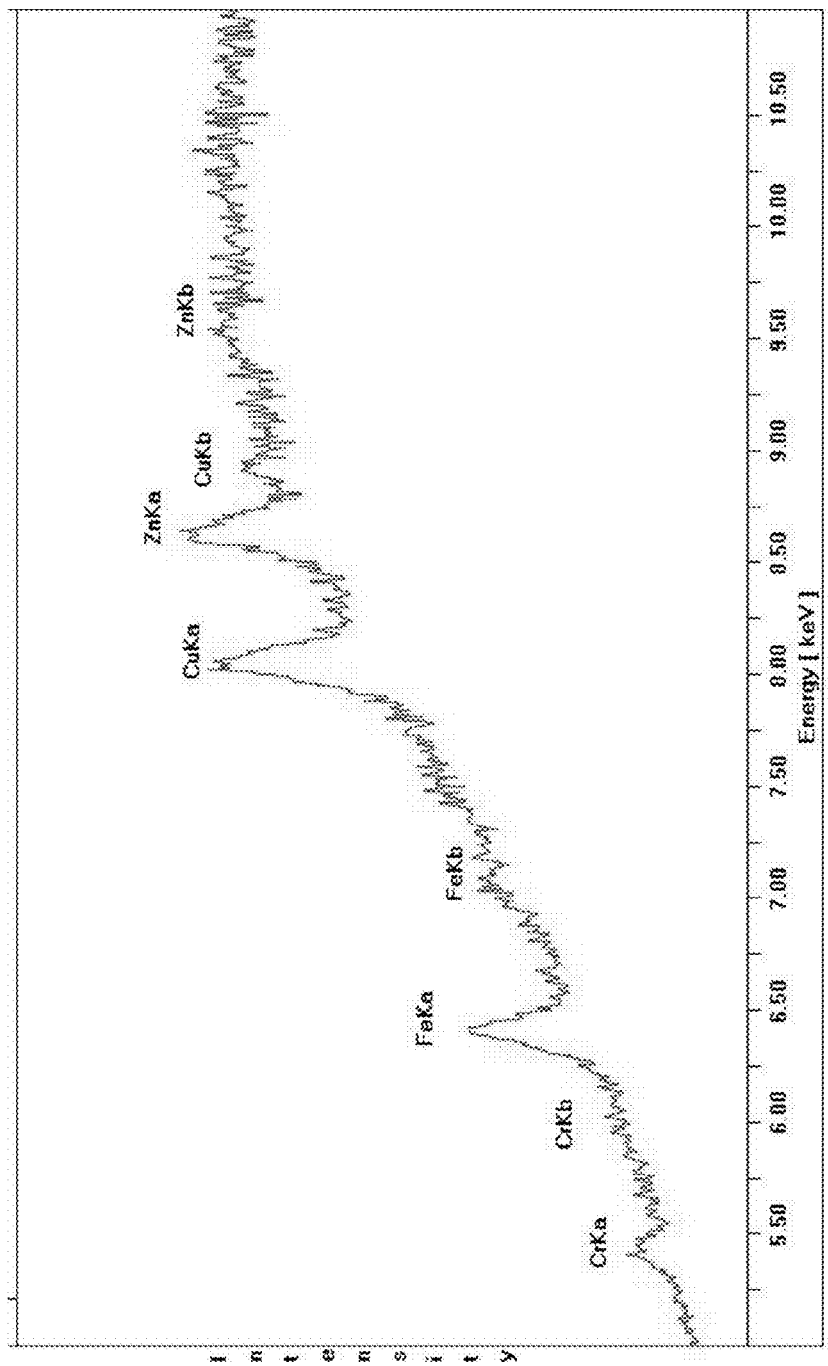
FIG. 12 shows spectrum of the cells exposed to chromium for one week, as described in Example 3.

Primary white melanocytes were cultured in normal culture medium with and without chromium (VI) for one week. The cells were washed with isotonic ammonium acetate buffer. Cells were air dry and resuspended in 20 mM glycine pH 2.8. Cells were then concentrated on spin plate for 2 hours at 75 degrees Celsius. FIG. 11 shows elemental spectrum of control cells not exposed to chromium, and FIG. 12 shows spectrum of the cells exposed to Cr for one week.

EXAMPLE 4

Figure 13:
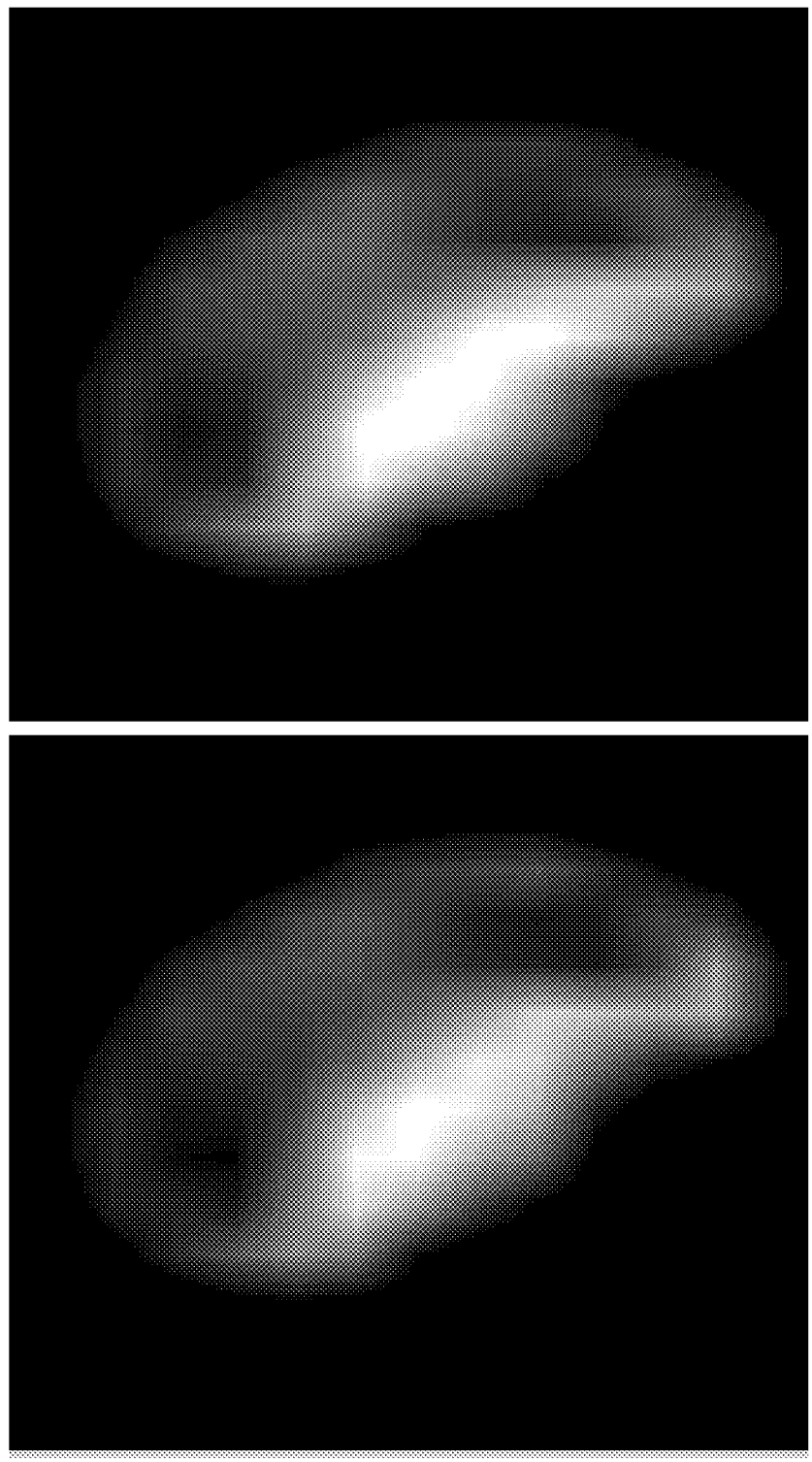
FIG. 13 shows a stereoview of a biological sample as described in Example 4.
Figure 14:
FIG. 14 shows an optical micrograph of a biological sample as described in Example 4.
Figure 15:
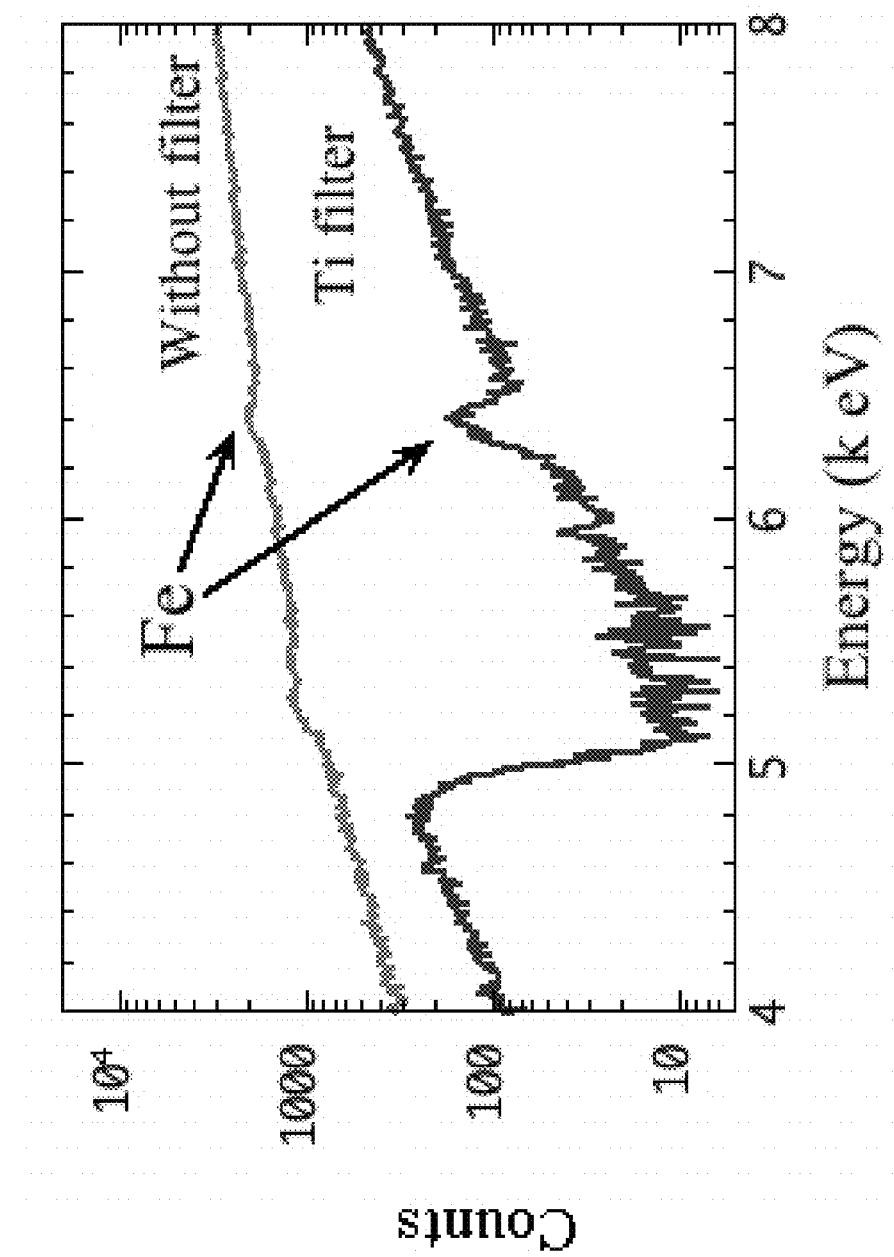
FIG. 15 shows an overlay of an X-ray fluorescence spectrum of human transferrin with and without a 25 micron titanium filter between the X-ray source and the sample, as described in Example 5.

FIG. 13 shows a 3D reconstruction of an X-ray fluorescence image analysis. A sample of pepperoni was analyzed to identify regions of element content heterogeneity. A 1 mm thick sample was mounted on polycarbonate. A rhodium tube was used for X-ray excitation and an energy dispersive silicon drift detector was used to simultaneously monitor phosphorus, sulfur, chlorine, potassium, calcium, scandium, titanium, vanadium, chromium, manganese, iron, cobalt, nickel, copper, and zinc X-ray fluorescence and rhodium elastic and inelastic scatter peaks. Two images were acquired that differ in the angle between the sample and the X-ray excitation beam by 15 degrees. Images were produced by taking the ratio of calcium to sulfur, spatially interpolating to smooth edges, normalizing and generating grey-scale bitmap images (FIG. 13) which were simultaneously adjusted for contrast and brightness to optimize viewing. For 3D visualization, the images are presented as a cross-eye stereo pair, in which the image intended for viewing by the left eye is placed on the right, and the image intended for viewing by the right eye is placed on the left. For correlative analysis, an image of the same region was also acquired using standard visible light microscope, as shown in FIG. 14. The stereoview X-ray fluorescence analysis shown in FIG. 13 identifies in three dimensions regions of sample that differ in their elemental composition and are not observable in light microscopy. A tumor sample could have been analyzed in the same manner.

EXAMPLE 5

A sample of dried human holo-transferrin was measured using an X-ray fluorescence spectrometer equipped with a rhodium tube for X-ray excitation and an energy dispersive silicon drift detector to simultaneously monitor phosphorus, sulfur, chlorine, potassium, calcium, scandium, titanium, vanadium, chromium, manganese, iron, cobalt, nickel, copper, and zinc X-ray fluorescence and rhodium elastic and inelastic scatter peaks. A spectrum was obtained without a filter disposed between the X-ray tube and the sample (upper spectrum in FIG. 15) and a spectrum was obtained with a 25 micron titanium filter disposed between the X-ray tube and the sample (lower spectrum in FIG. 15). The dead time without the filter was 30%, and the dead time with the filter was 15%.

The foregoing description of the invention has been presented for purposes of illustration and description and is not intended to be exhaustive or to limit the invention to the precise form disclosed, and obviously many modifications and variations are possible in light of the above teaching.

The embodiment(s) were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method to quantify biomarkers, comprising providing a sample comprising a biomarker, the biomarker comprising one or more chemicals that are related to a physiological condition; fractionating the sample to provide sample fractions; using an X-ray fluorescence spectrometer comprising an X-ray excitation source to perform an X-ray fluorescence analysis on a sample fraction to obtain spectral features derived from the biomarker; and quantifying the X-ray fluorescence signal of the biomarker; wherein the X-ray fluorescence spectrometer irradiates the sample fraction with polychromatic X-rays, and the X-ray fluorescence analysis comprises multiple X-ray fluorescence analyses obtained wherein the sample fraction is disposed at two or more different angles relative to the excitation source.

2. The method of claim 1, further comprising preparing the sample for X-ray fluorescence by exposing the sample to a solution.

3. The method of claim 1, further comprising homogenizing the sample prior to fractionating the sample.

4. The method of claim 1, wherein fractionating the sample is performed using a technique selected from the group of techniques consisting of centrifugation, mechanical separation, chemical separation, enzymatic separation, condensation, chromatographic methods, gel electrophoresis, isoelectric focusing, 2D electrophoresis, precipitation, density gradient fractionation and immobilization of analytes to solid formats.

5. The method of claim 1, wherein fractionating the sample comprises immobilization of analytes to solid formats wherein the solid formats are selected from the group consisting of beads, membranes, arrays, microarrays, spin plate, or well plates.

6. The method of claim 5, wherein fractionation comprises immobilization of analytes utilizing well plates.

7. The method of claim 1, wherein fractionation is performed by centrifugation.

8. The method of claim 1, wherein the sample fraction is disposed on or in a sample holder, and the sample holder comprises at least one chemical element which is not present in the sample.

9. The method of claim 1, further comprising the step of constructing a tomogram.

10. A method to diagnose abnormal conditions, comprising providing one or more clinical samples, the one or more clinical samples comprising a biomarker; fractionating the sample to provide sample fractions; using an X-ray fluorescence spectrometer comprising an X-ray excitation source to perform an X-ray fluorescence analysis on the sample fraction to obtain spectral features derived from at least one biomarker; and quantifying the X-ray fluorescence signal of the biomarker, wherein the X-ray fluorescence spectrometer irradiates the sample fraction with polychromatic X-rays, and the X-ray fluorescence analysis comprises multiple X-ray fluorescence analyses obtained wherein the sample fraction is disposed at two or more different angles relative to the excitation source.

11. The method of claim 10, further comprising exposing the sample to a solution to prepare the sample for the X-ray fluorescence analysis.

12. The method of claim 10, further comprising homogenizing the sample prior to fractionating the sample.

13. The method of claim 10, wherein fractionating the sample is performed using a technique selected from the group of techniques consisting of centrifugation, mechanical separation, chemical separation, enzymatic separation, condensation, chromatographic methods, gel electrophoresis, isoelectric focusing, 2D electrophoresis, precipitation, density gradient fractionation and immobilization of analytes to solid formats.

14. The method of claim 10, wherein fractionating the sample comprises immobilization of analytes to solid formats wherein the solid formats are selected from the group consisting of beads, membranes, arrays, microarrays, spin plate, or well plates.

15. The method of claim 14, wherein fractionation comprises immobilization of analytes utilizing well plates.

16. The method of claim 10, wherein fractionation is performed by centrifugation.

17. The method of claim 10, wherein the sample fraction is disposed on or in a sample holder, and the sample holder comprises at least one chemical element which is not present in the sample.

18. The method of claim 10, further comprising the step of obtaining data concerning the at least one of the one or more clinical samples using at least one other test.

19. The method of claim 18, further comprising the step of comparing the spectral features derived from the biomarker to data obtained from the at least one other test.

20. The method of claim 10, further comprising the step of constructing a tomogram.

21. A method to identify one or more abnormal portions of a sample, comprising fractionating a clinical sample to provide sample fractions; the clinical sample comprising normal and abnormal portions; disposing least one sample fraction in a sample holder; providing an X-ray fluorescence spectrometer, the X-ray fluorescence spectrometer comprising an X-ray excitation source; using the X-ray fluorescence spectrometer to perform an X-ray fluorescence analysis on the sample fraction to obtain spectral features derived from at least one biomarker; and using spectral features derived from the biomarker to determine whether at least one portion of the sample fraction is normal or abnormal, wherein the X-ray fluorescence is performed using excitation of the fractioned sample with polychromatic X-rays, and the X-ray fluorescence analysis comprises multiple X-ray fluorescence analyses obtained wherein the sample fraction is disposed at two or more different angles relative to the excitation source.

22. The method of claim 21, further comprising preparing the sample for X-ray fluorescence by exposing the sample to a solution.

23. The method of claim 21, further comprising the step of constructing a tomogram.

* * * * *